United States Patent
Lulla et al.

(10) Patent No.: US 7,395,821 B2
(45) Date of Patent: Jul. 8, 2008

(54) MULTI-DOSE INHALER

(75) Inventors: Amar Lulla, Maharashtra (IN); Geena Malhotra, Maharashtra (IN); Xerxes Rao, Maharashtra (IN)

(73) Assignee: Cipla Limited, Mumbai (IN)

( * ) Notice: Subject to any disclaimer, the term of this patent is extended or adjusted under 35 U.S.C. 154(b) by 187 days.

(21) Appl. No.: 10/563,770

(22) PCT Filed: Jul. 9, 2004

(86) PCT No.: PCT/GB2004/002982

§ 371 (c)(1),
(2), (4) Date: Feb. 27, 2006

(87) PCT Pub. No.: WO2005/004962

PCT Pub. Date: Jan. 20, 2005

(65) Prior Publication Data

US 2006/0237008 A1 Oct. 26, 2006

(30) Foreign Application Priority Data

Jul. 9, 2003 (IN) .................. 700/MUM/2003

(51) Int. Cl.
*A61M 15/00* (2006.01)

(52) U.S. Cl. ............... 128/203.12; 128/203.15; 128/204.13

(58) Field of Classification Search ............ 128/203.15, 128/203.21, 200.22, 200.21, 204.13, 203.12
See application file for complete search history.

(56) References Cited

U.S. PATENT DOCUMENTS

| | | | |
|---|---|---|---|
| 5,388,572 A * | 2/1995 | Mulhauser et al. ..... | 128/203.15 |
| 6,116,238 A * | 9/2000 | Jackson et al. ......... | 128/203.15 |
| 2002/0032409 A1* | 3/2002 | Ritsche ....................... | 604/154 |

\* cited by examiner

*Primary Examiner*—Steven O Douglas
(74) *Attorney, Agent, or Firm*—Dykema Gossett PLLC

(57) ABSTRACT

The present invention relates to an inhaler device and provides such a device comprising first and second compartments (4, 6) movable relative to one another such that, upon movement of said components (4, 6), operating means (16, 28, 40, 42, 44, 46) advances a cartridge compartment (140) into a predetermined position relative to medicament extraction facilitating means (14) and extends the medicament extraction facilitating means (14) into a position adjacent said advanced compartment (140) for allowing medicament extraction upon inhalation by a user.

43 Claims, 11 Drawing Sheets

MULTI-DOSE INHALER

BACKGROUND OF THE INVENTION

1. Field of the Invention

The present invention relates to inhalers for the administering of medicament, particularly multi-dose inhalers, and more particularly to inhalers which are used with pierceable sealed cartridges having a plurality of medicament compartments. Such inhalers allow for the administration of predetermined doses of medicament (typically a dry powder medicament).

2. The Prior Art

A wide variety of multi-dose inhalers are presently available on the market and they are designed for the inhalation of predetermined multiple doses of medicament by a patient. One example of a conventional inhaler has top and bottom portions enclosing a circular cartridge of medicament comprising a plurality of cavities in which predetermined quantities of medicament are held. A spike member, operable by a user (e.g. a patient), is pressed down by hand and pierces a foil sealingly the cartridge. A patient may then inhale medicament through a mouthpiece. Once inhalation of medicament from one cavity is completed, a fresh medicament cavity is brought to an inhalation position by manually lifting the spike and then rotating the top portion relative to the bottom portion. It will be understood that, in using this type of inhaler, a user must perform multiple operations. These multiple operations render conventional types of inhaler extremely inconvenient to use.

The present invention provides an inhaler device comprising first and second components movable relative to one another; means for receiving a medicament cartridge comprising a plurality of compartments containing medicament; medicament extraction facilitating means for locating adjacent a compartment of a received cartridge and thereby allowing an extraction of medicament therefrom; and operating means which, when activated by a user, advances a cartridge compartment of a received cartridge into a predetermined position relative to the medicament extraction facilitating means and extends the medicament extraction facilitating means into a position adjacent said advanced compartment for allowing medicament extraction upon inhalation by a user; wherein the operating means is mounted relative to said first and second components so as to be activated in response to said first and second components being moved relative to one another by a user.

It will be understood therefore that, in use of an inhaler device according to the present invention, a user moves first and second components relative to one another and, in so doing, advances a cartridge compartment containing medicament into an appropriate position relative to medicament extraction facilitating means, such as a spike, and also extends the medicament extraction facilitating means into a position allowing medicament to be extracted from the advanced compartment. Accordingly, as a result of a single action by the user, multiple operations are undertaken within the inhaler device. As such, the inhaler device according to the present invention is very convenient to use.

Embodiments of the present invention will now be described with reference to the accompanying drawings.

DETAILED DESCRIPTION OF THE PREFERRED EMBODIMENTS

Figure 1:
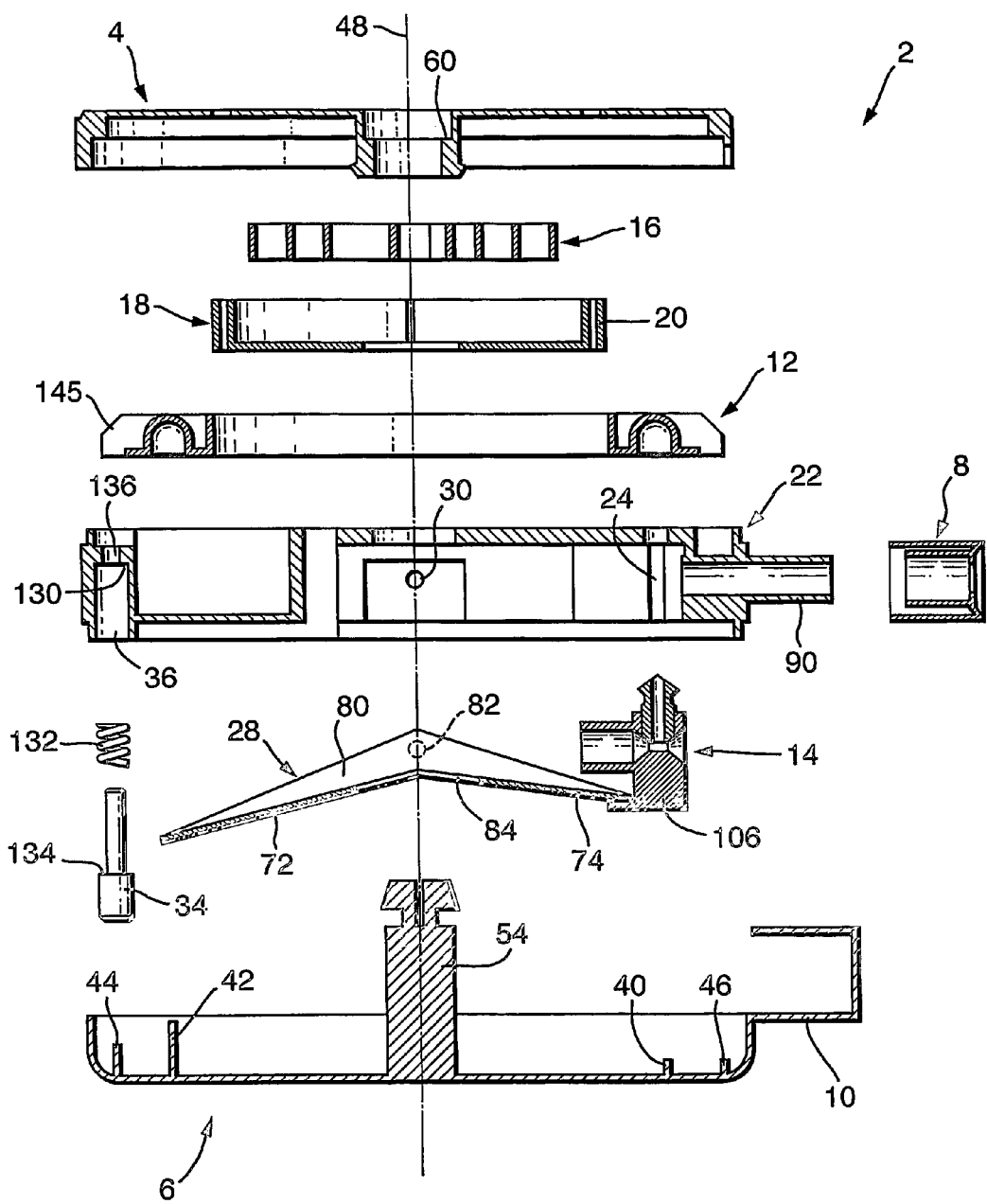
FIG. 1 is an exploded cross-sectional side view of an inhaler device according to the present invention.

An exploded cross-sectional side view of an inhaler device 2 according to the present invention is shown in FIG. 1 of the accompanying drawings. The inhaler device 2 comprises a top body portion 4 and a bottom body portion 6 which snap-fit together to form a circular disc-shaped body from which a mouthpiece 8 and mouthpiece cover 10 radially project and in which remaining components of the inhaler device 2 are housed. As is discussed in greater detail below, the mouthpiece 8 is secured relative to the top body portion 4 whilst the mouthpiece cover 10 is secured relative to the bottom body portion 6. The mouthpiece cover 10 may be manufactured separately to the bottom body portion 6 and attached thereto by means of resilient snap-fitting attachment means. However, in the illustrated embodiment, the mouthpiece cover 10 is provided integrally with the bottom body portion 6.

The attachment of the top and bottom body portions 4, 6 is such that the body portions 4, 6 are permitted to rotate relative to one another so that the mouthpiece cover 10 can be moved between a mouthpiece covered position, in which the mouthpiece cover 10 occludes the mouthpiece 8 and provides a storage configuration for the inhaler device 2, and a mouthpiece uncovered position, in which the mouthpiece cover 10 is circumferentially spaced from the mouthpiece 8 so as to open the mouthpiece 8 and allow a subsequent inhalation of medicament.

When a user of the inhaler device 2 rotates the top and bottom body portions 4, 6 relative to one another from the aforementioned storage position to the aforementioned use position, a circular disc-shaped cartridge 12 comprising multiple doses of medicament is automatically rotated so that a compartment containing the next dose of medicament to be administered is first moved into alignment with medicament extraction facilitating means, such as a spike 14 (as shown in the accompanying drawings), and then pierced by said spike 14. A user may subsequently inhale the dose of medicament held within the pierced compartment via the uncovered mouthpiece 8.

When the user rotates the top and bottom body portions 4, 6 relative to one another from the aforementioned use position to the aforementioned storage position, the spike 14 is automatically retracted from the pierced compartment and the cartridge 12 is automatically further advanced so that the current number of unused doses of medicament is displayed in a window in the top body portion 4. The inhaler device 2 therefore provides an extremely convenient and user-friendly means for administering a dose of medicament by inhalation.

The various components referred to above as being housed between the top and bottom body portions 4, 6 include a spiral torsion spring 16 which, primarily for the convenience of assembly, is held within a circular dish-shaped spring drum member 18. The aforementioned medicament cartridge 12 is of an annular shape and the inner diameter thereof is approximately the same as the outer diameter of the spring drum member 18. The relative geometries of these components 16, 18, 12 are such that, in the assembled inhaler device 2, the torsion spring 16 is located within an annular upstanding wall 20 of the spring drum member 18 and the drum member 18 is located in the circular space defined by the annular cartridge 12. As will be described hereinafter, means (the spring drum member 18) are provided for fixing the radially outer end of the torsion spring 16 to the cartridge 12 and the distal radially inner end of the spring 16 to the top body portion 4. It will be understood that the inner and outer ends of the spring 16 are fixed to the top body portion 4 and drum member 18 respectively in as much as said ends loop about these components so as to be retained thereagainst (i.e. the ends are not necessarily bonded to said components). In this way, the drum member 18 may be rotated relative to the top body portion 4 during the assembly of the inhaler device 2 so as to appropriately wind the torsion spring 16. As a consequence, said spring 16 applies a rotary biasing force tending to rotate the cartridge 12 relative to the top body portion 4 in a direction opposite to the direction of winding. As will be better understood from the following description, the torsion spring 16 thereby provides a driving force which allows medicament dose compartments to be moved into alignment with the spike 14.

However, in a yet further embodiment, a stop member is provided at 192 on the cartridge 12 for engaging a stop member at 193 on the top body portion 4 and/or central body portion 22. When these cartridge and body stop members engage with one another, rotation of the cartridge 12 relative to the body is prevented. The arrangement is such that the cartridge 12 may complete one full rotation or a sufficient rotation for all medicament doses to be administered, after which further rotation is prevented. A particular arrangement for these stop members is recited below during a detailed description of the cartridge 12.

It will be appreciated that, when the body stop member is provided on the top body portion 4, rotation of the cartridge 12 in winding the spring 16 during the assembly process will be hindered by the body and cartridge stop members engaging with one another. In these circumstances, it is preferable for the cartridge member 12 and drum member 18 to be separate components (rather than an integral component as mentioned above) and for the drum member 18 alone to be rotated when winding the spring 16. Once the spring 16 has been wound, the cartridge is then placed in engagement with the drum member 18.

Further components housed between the top and body portions 4, 6 include a central body portion 22 which, in the assembled inhaler device 2, is fixed relative to the top body portion 4 and provides a mounting point for the mouthpiece 8 and a number of other mounting points or linear guide ways for internal components associated with the aforementioned automatic indexing and piercing of medicament dose compartments and which components rotate or slide linearly within the inhaler body. Specifically, these moving components are the aforementioned spike 14 which is linearly slidable within oppositely positioned grooves 24, 26 in the central body portion 22 (see FIG. 11), a lever 28 which is pivotally located in oppositely positioned recesses or slots 30, 32 (ideally rectangular or circular holes) in the central body portion 22 and operates to retract the spike 14 from a pierced medicament dose compartment (see FIG. 11), and two identical spring biased pins 34 which are each linearly slidable within a cylindrical guide way 36, 38 defined in the central body portion 22 (see FIG. 11). As will be evident from the following description, the spike 14, lever 28 and pins 34 are moved relative to the central body portion 22 as a result of each of their engagement with a different one of four camming members 40, 42, 44, 46 upstanding from the bottom body portion 6. Each camming member is arranged lengthwise on a part-circular or circular line centred on the axis 48 of relative rotation of the top and bottom body portions 4, 6 and the cartridge 12. It will be understood therefore that, when the top body portion 4 and the bottom body portion 6 are rotated relative to one another, the spike 14, lever 28 and pins 34 follow their respective camming members 40, 42, 44, 46 and are moved appropriately so as to advance and pierce a medicament dose compartment.

The components of the inhaler device 2 illustrated in FIG. 1 will now be individually described in greater detail with reference to the first twenty of the accompanying drawings.

Figure 2:
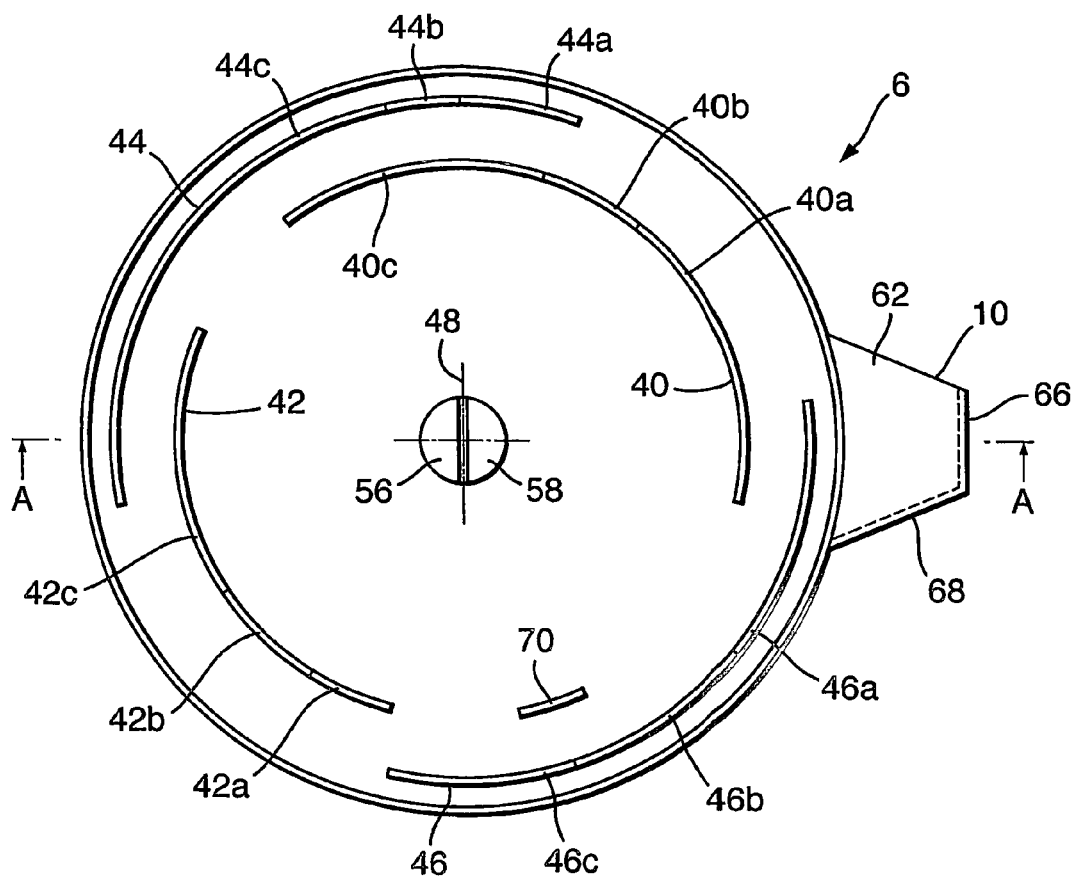
FIG. 2 is a top plan view of a bottom body portion of the inhaler device shown in FIG. 1.
Figure 3:
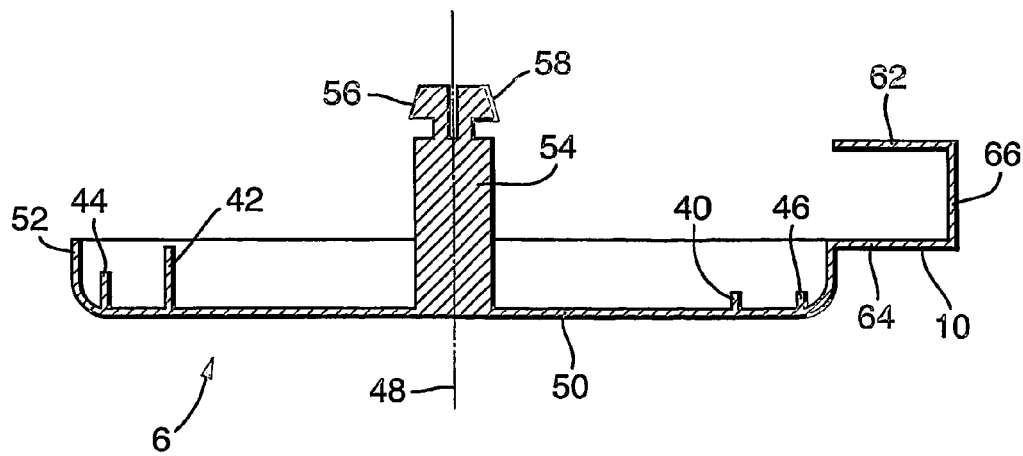
FIG. 3 is a cross-sectional side view of the bottom body portion of FIG. 2 taken along line A-A of FIG. 2.

With reference to FIGS. 2 and 3 of the accompanying drawings, it will be seen that the bottom body portion 6 has a circular planar base 50 with an annular wall 52 upstanding from the perimeter thereof. A cylindrical stud 54 also projects upwardly from the centre of the base 50 and, in the assembled inhaler device 2, the stud 54 projects through apertures in (i) the lever 28, (ii) the central body portion 22, and (iii) the cartridge 12, portion spring 16 and spring drum member 18 assembly, so as to snap-fit into the centre of the top body portion 4. The snap-fitting of the top and bottom body portions 4, 6 is facilitated by a conventional type of clip fastening comprising two shoulder members 56, 58 which project radially outwardly from an upper end of the stud 54 and which may be resiliently pressed radially inwardly towards one another. In the assembled inhaler device 2, the shoulder members 56, 58 latch onto an upwardly facing annular shoulder 60 provided on the top body portion 4. The arrangement is such that the top and bottom body portions 4, 6 may be rotated relative to one another about the axis 48.

The mouthpiece cover 10 projects radially from the perimeter wall 52 of the bottom body portion 6 by a distance sufficient to allow the cover 10 to be moved over the mouthpiece 8 when the top and bottom body portions 4, 6 are rotated relative to one another. The mouthpiece cover 10 comprises a top surface 62, a bottom surface 64, an end surface 66 and one side surface 68. A second side surface opposite the first side surface 68 is not provided so as to allow the mouthpiece 8 to slide sideways into the interior of the mouthpiece cover 10 upon relative rotation of the top and bottom body portions 4, 6. It will be understood that relative rotation of the top and bottom body portions 4, 6 will be limited in one rotary direction by an abutment of the mouthpiece 8 with the one side surface 68 of the mouthpiece cover 10. As will be understood more fully from the following description, relative rotation of the top and bottom body portions 4, 6 in the opposite rotary direction is limited by an abutment of the lever 28 with a stop projection 70 upstanding from the base 50 of the bottom body portion 6.

The aforementioned four camming members 40, 42, 44, 46 also project upwardly from the base 50 of the bottom body portion 6. Each camming member 40, 42, 44, 46 follows a part-circular line centred on the rotary axis 48. The radial distance of each camming member from the rotary axis 48 is such that each camming member locates below its respective component to be cammed (i.e. one of the spike 14, lever 28, and pins 34). In the illustrated embodiment, two camming members 44, 46 are located at the same radial distance from the rotary axis 48 and are circumferentially offset relative to one another so as to each cam a different one of the pins 34. Similarly, the remaining two camming members 40, 42 are located radially inwardly of the other two camming members 44, 46. These camming members 40, 42 are again circumferentially offset relative to one another and are located at the same radial distance from the rotary axis 48. The radial and circumferential positioning of these camming members 40, 42 is such that one of said camming members 40 locates so as to cam the spike 14 and the other one of said camming members locates so as to cam the lever 28 during use of the inhaler device 2.

In order for the stop projection 70 to conveniently limit rotary movement of the top and bottom body portions 4, 6 by abutting the lever 28, the stop projection 70 has the same radial spacing from the rotary axis 48 as the camming member 42 associated with the lever 28. The stop projection 70 is again circumferentially offset relative to the camming members 40, 42 having the same radial spacing from the rotary axis 48 and is circumferentially positioned so as to provide a predetermined degree of relative rotary motion between the top and bottom body portions 4, 6. In the inhaler device 2 shown in the accompanying drawings, the stop projection 70 is circumferentially positioned so that the top and body portions 4, 6 may move approximately 90° relative to one another between a storage configuration, in which the mouthpiece 8 is closed by the mouthpiece cover 10, and a use configuration in which the mouthpiece cover 10 is located to one side of the mouthpiece 8 so as to open the mouthpiece 8.

Although camming members 40, 42, 44, 46 and the stop projection 70 are provided in the illustrated embodiment with common radial positions, it will be understood that the inhaler device 2 can be arranged so that they all have different radial positions.

Figure 3A:
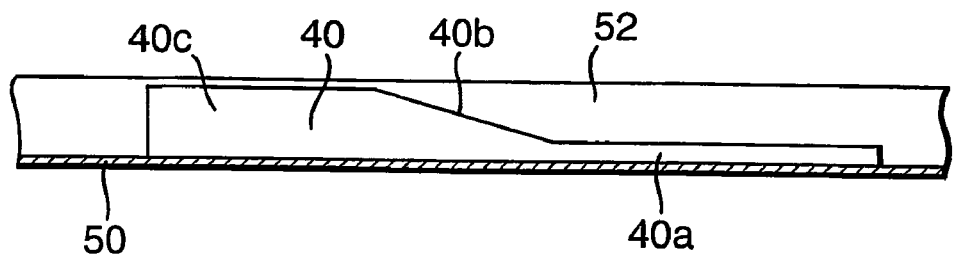
FIG. 3a is an unwrapped side profile view of a camming member of the bottom body portion of FIG. 3.

The camming members 40, 42, 44, 46 each operate in use to move an associated component of the inhaler device 2 between an extended position and a retracted position. Movement of the respective component between these positions is in a direction parallel with the rotary axis 48 (perpendicular to the planar base 50 of the bottom body portion 6). In order to move an associated component, each camming member comprises a low portion "a", a sloping portion "b", and a high portion "c". The low and high portions a, c are connected by means of the sloping portion b. An unwrapped side profile of the camming member 40 associated with the spike 14 is shown in FIG. 3a by way of example. The other canning members 42, 44, 46 have a similar profile to that of the camming member 40 shown in FIG. 3a, although the circumferential span of the low, sloping and high portions a, b, c of the camming members is as indicated in FIG. 2.

It will be understood that the purpose of the sloping portion b of each camming member is to provide a controlled camming of an associated component between extended and retracted positions at a particular angular orientation of the top body portion 4 relative to the bottom body portion 6. It will be understood from the following description regarding the operation of the inhaler device 2 that the relative angular positions of the sloping portions 40b, 42b, 44b, 46b of the camming members are critical in ensuring a retraction and extension of the associated components in a coordinated fashion which allows appropriate indexing and piercing of a medicament dose compartment. In this regard, reference should be made to the following description associated with FIGS. 21 and 22.

The stop projection 70 extends from the base 50 of the bottom body portion 6 to a similar extent as a high portion c of a camming member so as to ensure abutment with the lever 28.

Figure 4:
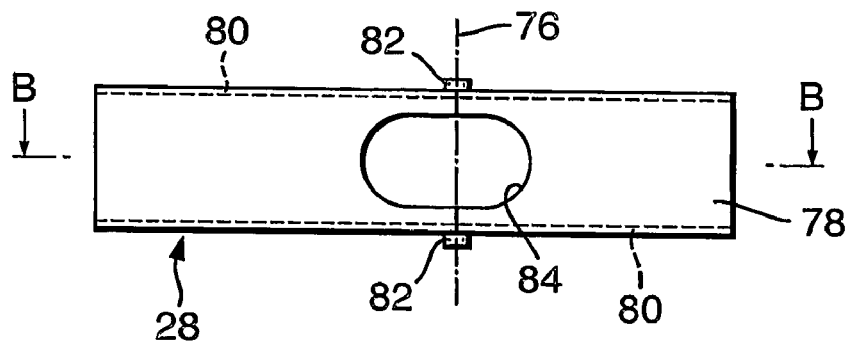
FIG. 4 is a bottom plan view of a lever of the inhaler device shown in FIG. 1.
Figure 5:
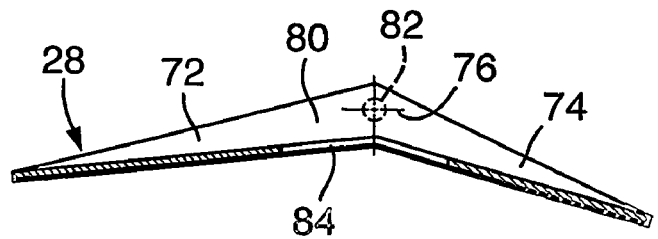
FIG. 5 is a cross-sectional side view of the lever of FIG. 4 taken along line B-B of FIG. 4.

With reference to FIGS. 4 and 5 of the accompanying drawings, it will be seen that the lever 28 comprises first and second elongate portions 72, 74 which interconnect with one another at fulcrum axis 76. The lever portions 72, 74 are oriented at a suitable angle relative to one another so as to ensure an effective camming action by the lever camming member 42. The first and second lever portion 72, 74 combine to form a lower lever surface 78 having an elongate rectangular platform. A sidewall 80 extends upwardly from each longer side of the lower surface 78. A boss 82 projects laterally outward from each sidewall 80 in line with the lever fulcrum axis 76. Furthermore, an aperture 84 is provided in the lower lever surface 78 through which the stud 54 of the bottom body portion 6 passes in the assembled inhaler device 2. The aperture 84 is oval or otherwise elongate in shape so as to prevent the stud 54 from restricting rotation of the lever 28 about the fulcrum axis 76.

In the assembled inhaler device 2, the bosses 82 of the lever 28 locate in a snap-fit fashion within the lever recesses 30, 32 of the central body portion 22. In use, a lever 28 rotates in a first direction within the lever recesses 30, 32 as the spike 14 is cammed to an extended position by the sloping portion 40b of the spike canning member 40, and in an opposite second direction when the lever first portion 72 is moved to an extended position by the sloping portion 42b of the lever camming member 42.

In the assembled inhaler device 2, the lower surface of the first lever portion 72 engages the sloping and high lever camming portions 42b, 42c whilst the lower surface of the second lever portion 74 engages the spike 14. It will be understood from the following description that the primary purpose of the lever 28 is to move the spike 14 from an extended position, in which the spike 14 penetrates a medicament dose compartment, to a retracted position, in which the spike 14 is spaced from the medicament cartridge 12 so that said cartridge 12 may rotate and a fresh dose of medicament thereby appropriately advanced.

It is to be emphasised that the spike 14 is moved from the extended position to the retracted position by means of a canning action on the lever 28 rather than by a spring biasing means (such as a helical compression spring) as is the case for the pins 34. Although spring biasing means can be used in respect of the spike 14, the advantages of both extending and retracting the spike 14 by means of a camming action are twofold. Firstly, the force applied to the spike 14 in moving the spike 14 from the extended position to the retracted position is not limited by the biasing force of the biasing means (which, in the case of a compression spring, is dependent upon the extent of compression and reduces with the extent of compression). Thus, the possibility of the spike 14 becoming held in the extended position by, for example, material pierced by the spike 14 is significantly reduced. A second advantage of the dual camming action is that the relative angular positions of the top and bottom body portions 4, 6 when the spike 14 (i) begins to move from the fully retracted position and (ii) finally locates back in the fully retracted position, may be made to be different and, similarly, the relative angular positions of the top and bottom body portions 4, 6 when the spike 14 (i) first locates in the fully extended position and (ii) begins to move from the fully extended position, may be made to be different. This can be beneficial in coordinating the piercing and indexing functions.

Figure 9:
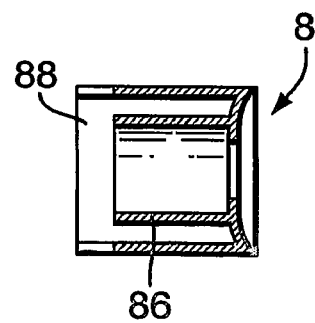
FIG. 9 is a cross-sectional side view of the mouthpiece of FIG. 8 taken along line D-D of FIG. 8.
Figure 10:
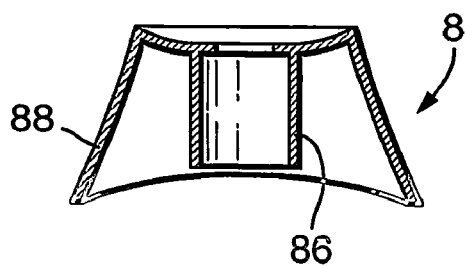
FIG. 10 is a cross-sectional bottom view of the mouthpiece of FIG. 8 taken along line E-E of FIG. 8.

The mouthpiece 8 as shown in FIGS. 9 to 10 of the accompanying drawings comprises an inner tube 86 concentrically arranged within and connected to an outer tube 88. The inner tube 86 is shaped and sized so as to locate with an interference fit over a radially extending tube 90 of the central body portion 22. Any other suitable means may be used to attach the mouthpiece to the tube. The outer tube 88 of the mouthpiece 8 is shaped and sized so that the mouth of a user may form a convenient and comfortable seal with the inhaler device and thereby facilitate ready inhalation of a medicament dose.

Figure 6:
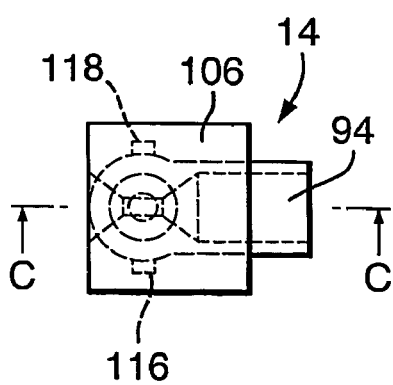
FIG. 6 is a bottom plan view of medicament extraction facilitating means (e.g. a spike) of the inhaler device shown in FIG. 1.
Figure 7:
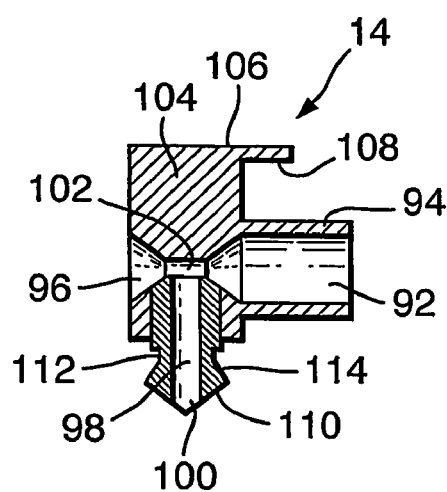
FIG. 7 is a cross-sectional side view of the medicament extraction facilitating means of FIG. 6 taken along line C-C of FIG. 6.
Figure 8:
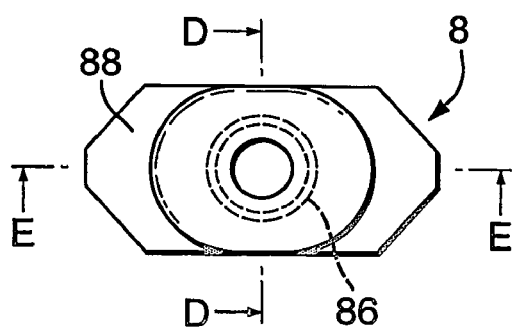
FIG. 8 is a front view of a mouthpiece of the inhaler device shown in FIG. 1.

The spike 14 is shown in FIGS. 6 and 7 of the accompanying drawings. The spike 14 defines a T-shaped fluid passageway which is made up of a first fluid passageway 92 having an inlet 94 and an outlet 96, and a second fluid passageway 98 having an inlet 100 and joining with the first fluid passageway 92 at a restriction 102 in the first fluid passageway 92. It will be understood that, during use of the inhaler device 2, the inhalation of a user draws air through the first fluid passageway 92 from the inlet 94 to the outlet 96 through the restriction 102. It will be further understood that the restriction 102 provides a venturi and reduces the local static fluid pressure. As a result, fluid is encouraged to flow through the second fluid passageway 98 from the inlet 100. When the mouthpiece 8 is uncovered and ready for use, the inlet 100 is located within a pierced dose compartment and, as such, fluid flowing from the inlet 100 through the second fluid passageway 98 and into the mouthpiece 8 via the outlet 96 tends to be entrained with medicament (dry powdered medicament) contained in the pierced dose compartment. It will be appreciated that the restriction 102 is optional; however, since it eases inhalation of medicament, it is considered to be a preferred feature.

The T-shaped fluid passageway is defined in a body 104. The body 104 has a camming surface 106 which is engaged by the spike camming member 40. A further surface 108 of the spike body 104 is provided to be engaged by the second portion 74 of the lever 28 during use of the inhaler device 2. This surface 108 is pressed by the lever 28 so as to retract the spike 14.

With reference to FIG. 7 it will be seen that the portion 110 of the spike 14 which in use pierces a medicament dose compartment is provided as a separate component which is connected to the remainder of the spike body 104. Whilst the spike body 104 can be made as a unitary component, the provision of the piercing portion 110 as a separate component allows the piercing portion 110 to be made of a different material to the remainder of the spike body 104. Ideally, the piercing portion 110 is manufactured from a hardwearing metallic material whilst the remainder of the spike body 104 is manufactured from a plastics material. The leading end of the piercing portion 110 has a conical shape which is effective at piercing a dose compartment. A circumferential groove 112 is provided in the piercing portion 110 adjacent to the leading piercing end thereof. A frustro-conical surface 114 is located between the leading piercing end and the circumferential groove 112. The frustro-conical surface 114 operates in use to cam pierced material (for example, foil) of a dose compartment axially along the length of the piercing portion 110 and into the circumferential groove 112. In this way, the piercing process is improved and a more effective seal between the pierced material and the piercing portion 110 is provided. As such, the efficiency of a user's inhalation in extracting medicament is improved.

With reference to FIG. 6 of the accompanying drawings, it will be seen that the spike body 104 is provided with two elongate projections 116, 118 which extend longitudinally in a direction parallel with the longitudinal axis of the piercing portion 110. The projections 116, 118 respectively locate in grooves 24, 26 of the central body portion 22 and thereby constrain movement of the spike 14 to a linear movement between the extended and retracted positions. In other words, the projections 116, 118 slide along the grooves 24, 26 in use and thereby limit undesirable movements of the spike 14.

Figure 11:
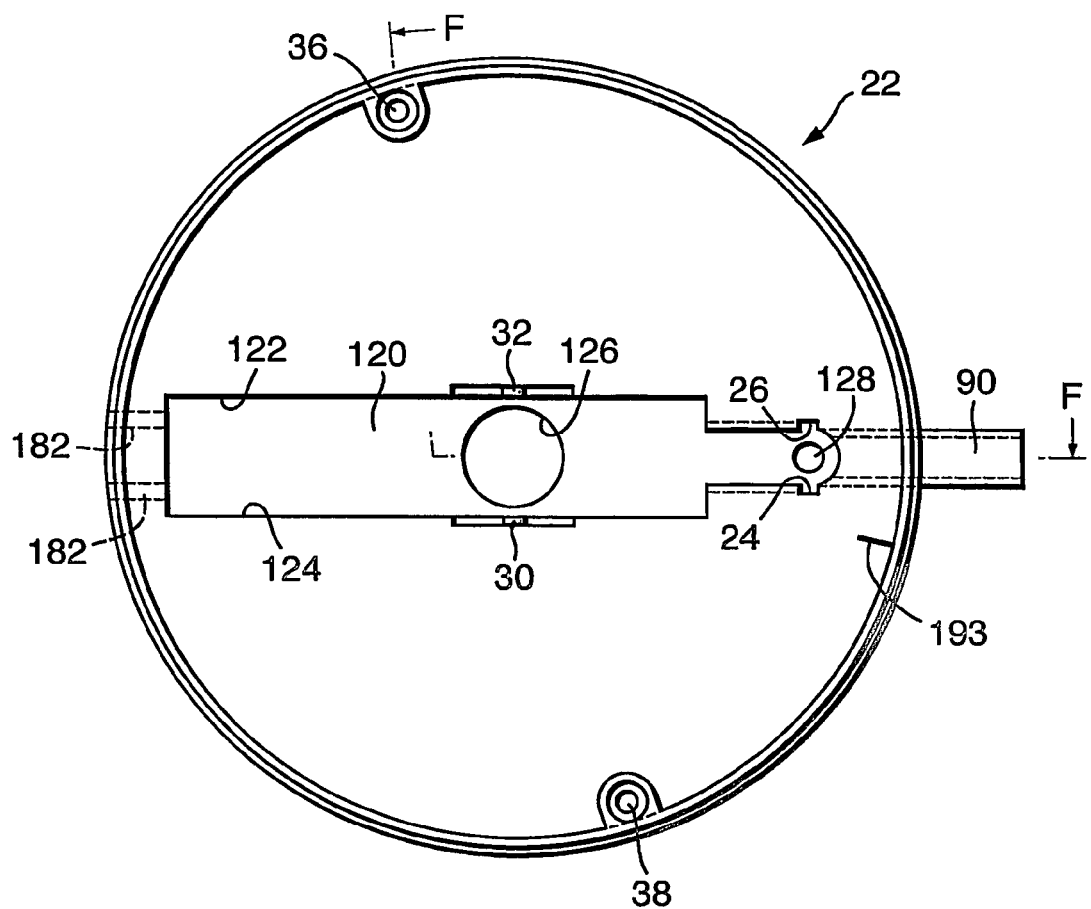
FIG. 11 is a top plan view of a central body portion of the inhaler device shown in FIG. 1.
Figure 12:
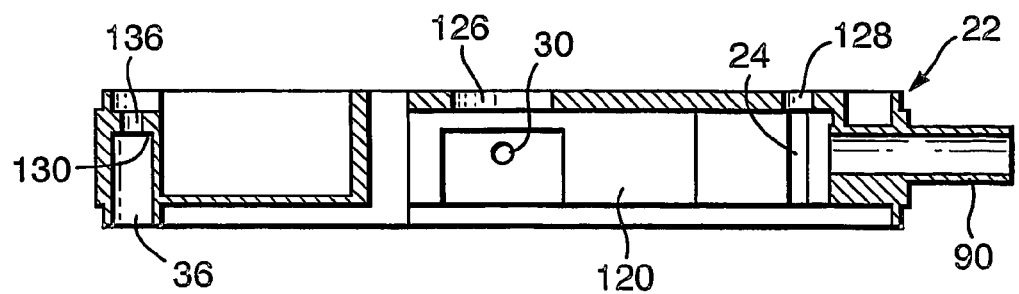
FIG. 12 is a cross-sectional side view of the central body portion of FIG. 11 taken along line F-F of FIG. 11.
Figure 13:
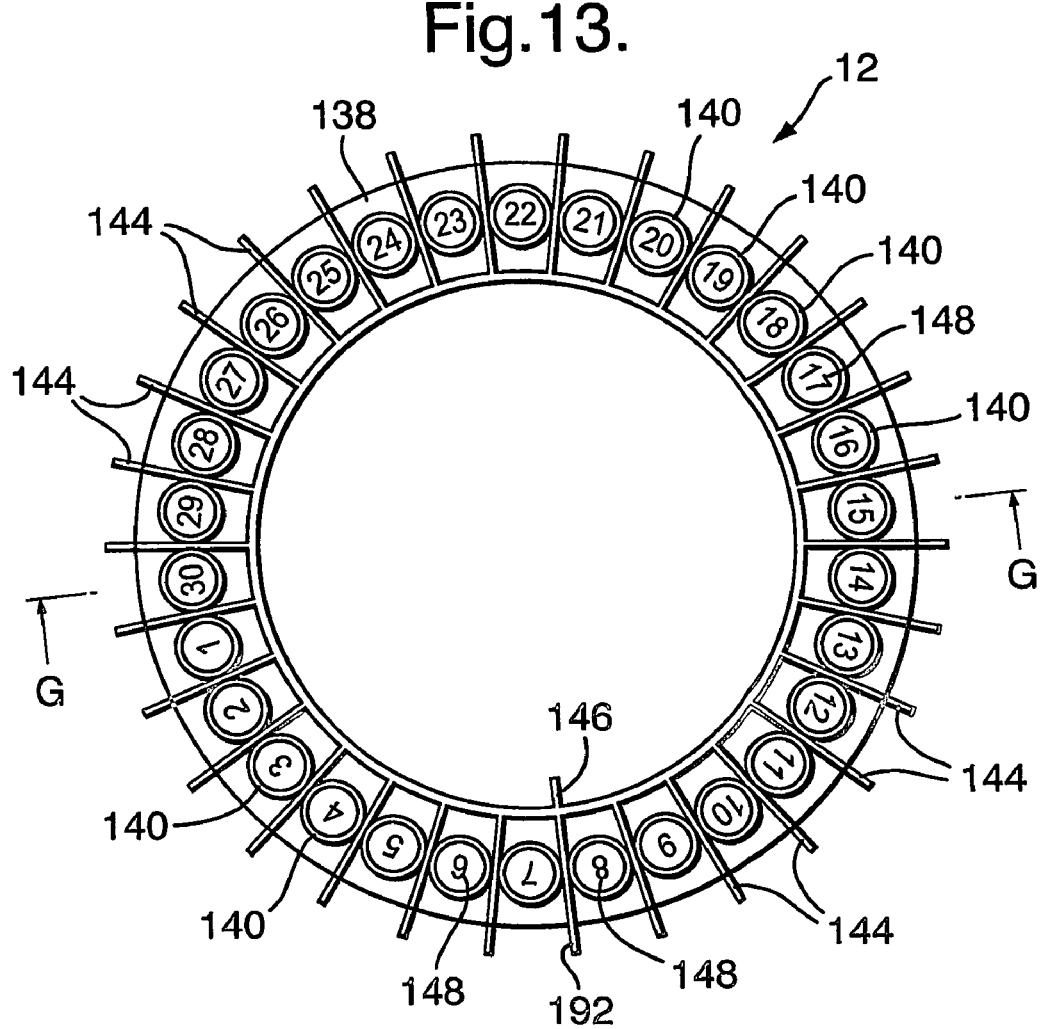
FIG. 13 is a top plan view of a medicament cartridge of the inhaler device shown in FIG. 1.
Figure 14:
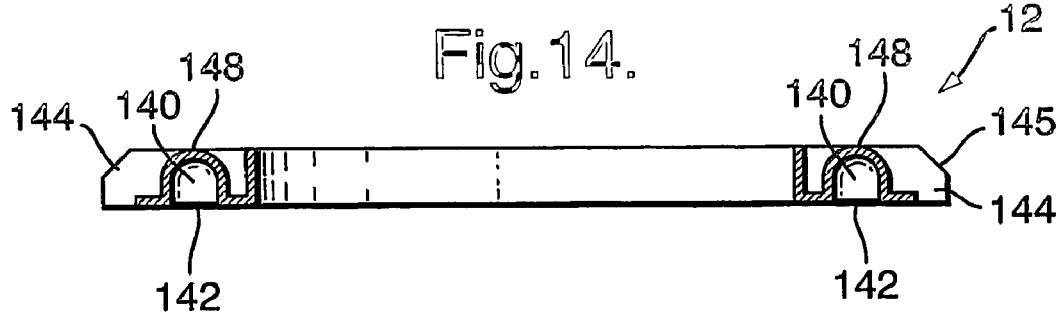
FIG. 14 is a cross-sectional side view of the medicament cartridge of FIG. 13 taken along line G-G of FIG. 13.

With reference to FIGS. 11 and 12, it will be seen that the central body portion 22 is a circular disc-shaped component having a central diametrically extending recess 120 in which the lever 28 and spike 14 locate. The aforementioned recesses 30, 32 and grooves 24, 26 are provided in side walls 122, 124 of the groove 120. An aperture 126 centred on the rotary axis 48 is provided in the central body portion 22. In the assembled inhaler device 2, the stud 54 of the bottom body portion 6 extends through the aperture 126. A further aperture 128 is also provided in the central body portion 22 through which, in use, the piercing portion 110 projects when the spike 14 is extended.

It will also be seen from FIGS. 11 and 12 that the central body portion 22 defines the aforementioned two cylindrical pin guide ways 36, 38. Each guide way 36, 38 comprises an annular shoulder 130 against which a helical compression spring 132 (see FIG. 1) for biasing the associated pin 34 abuts. Each pin 34 also comprises an annular shoulder 134 (see FIG. 1) against which the associated compression spring 132 abuts. The annular shoulder 130 in each pin guide way 36, 38 defines a yet further aperture 136 through which, in the assembled inhaler device, the associated pin 34 projects. It will be understood that the compression spring 132 presses against each annular shoulder 130, 134 so as to ensure the associated pin 34 remains in contact with the associated pin camming member 44, 46. The spring 32 ensures that the associated pin 34 remains in contact with at least one of the portions a, b, c of the associated pin camming member at all times.

The medicament cartridge 12 comprises an annular body 138 housing a plurality of compartments 140 for storing a dose of medicament. Each compartment 140 has a portion which can be pierced by the spike 14. In the cartridge 12 shown in the accompanying drawings, a total of thirty medicament dose compartments 140 are arranged in a circle and formed integrally with the cartridge body 138. A cartridge comprising a different number of dose compartments may of course be provided. A lower side of each compartment 140 is left open when manufacturing the cartridge 138 so as to allow each compartment 140 to be filled with an appropriate dose of medicament. Once each compartment 140 has been filled with medicament, each compartment 140 is sealingly closed by means of a piercable material 142 (for example, metallic foil). The piercable material may be secured to the cartridge body 138, so as to sealingly close each compartment 140, by suitable means such as an adhesive applied to the perimeter of each compartment opening or a heat sealing technique. In use of the inhaler device 2, the piercing portion 110 of the spike 14 pierces the piercable material 142 and extends through the opening of the associated compartment 140 into close proximity of the medicament contained within said compartment.

The cartridge body 138 further comprises thirty projections 144 (i.e. one projection 144 for each compartment 140). One projection may be arranged in an extended position so as to provide a cartridge stop member as mentioned above. The structure of each of the projections 144 is such that they each have a slant upper surface 145 which corresponds to a slant lower surface of the stop member at 193 on the top body portion 4. The projections 144 may thereby move past the stop member at 193. However, one projection 144 at 192 may be characterised with the absence of such a slant portion so as to provide a stop member for abutting the member at 193. Each projection 144 extends radially from the outer circumference of the annular body portion. Each projection 144 is further circumferentially located between adjacent compartments 140. The projections 144 are, in use, engaged and disengaged by the pins 34 in a coordinated fashion controlled by the pin camming members 44, 46 so as to ensure that the cartridge 12 is advanced (under the biasing action of the spiral torsion spring 16) by a single compartment 140 each time the mouthpiece 8 is opened and closed by the mouthpiece cover 10. As will be appreciated from the forthcoming description of this indexing process, the circumferential thickness and spacing of the cartridge projections 144 on the one hand and the diameter of the pin 34 on the other hand is critical in ensuring that the cartridge 12 is able to advance. It will be understood that, if the diameter of the pins 34 relative to the circumferential spacing of the projections 144 is too great, then the cartridge 12 will be unable to advance (see FIGS. 21 and 22).

In addition to the cartridge projections 144 which extend radially outwardly from the outer circumference of the annular body 138, a further singular projection 146 extends radially inwardly from the inner circumference of the annular body 138. The purpose of the further projection 146 is merely to engage with a corresponding recess 147 in the outer surface of the annular wall 20 of the spring drum member 18 and thereby prevent relative rotary movement between the cartridge 12 and the spring drum member 18 (see FIG. 15).

Finally with regard to the cartridge 12, the side of each compartment 140 opposite to the side provided with piercable material is ascribed with indicia 148 specific to the dose of medicament contained within the associated compartment 140. In the cartridge 12 shown in the accompanying drawings, the array of 30 compartments 140 are numbered consecutively from 1 to 30 and the indicia 18 indicates the number of a particular compartment 140. When the mouthpiece 8 is covered by the mouthpiece cover 10 in the assembled inhaler device 2, the indicia 148 is visible to a user through a window or aperture 150 in the top body portion 4 and, in the inhaler device 2 shown in the accompanying drawings, the indicia 148 thereby indicates to the user the number of compartments 140 which have not as yet been used and which remain filled with medicament to be inhaled. Each time the mouthpiece 8 is opened and closed with the mouthpiece cover 10, the cartridge 12 advances by one compartment 140 and the number shown in the window 150 reduces by one.

Figure 15:
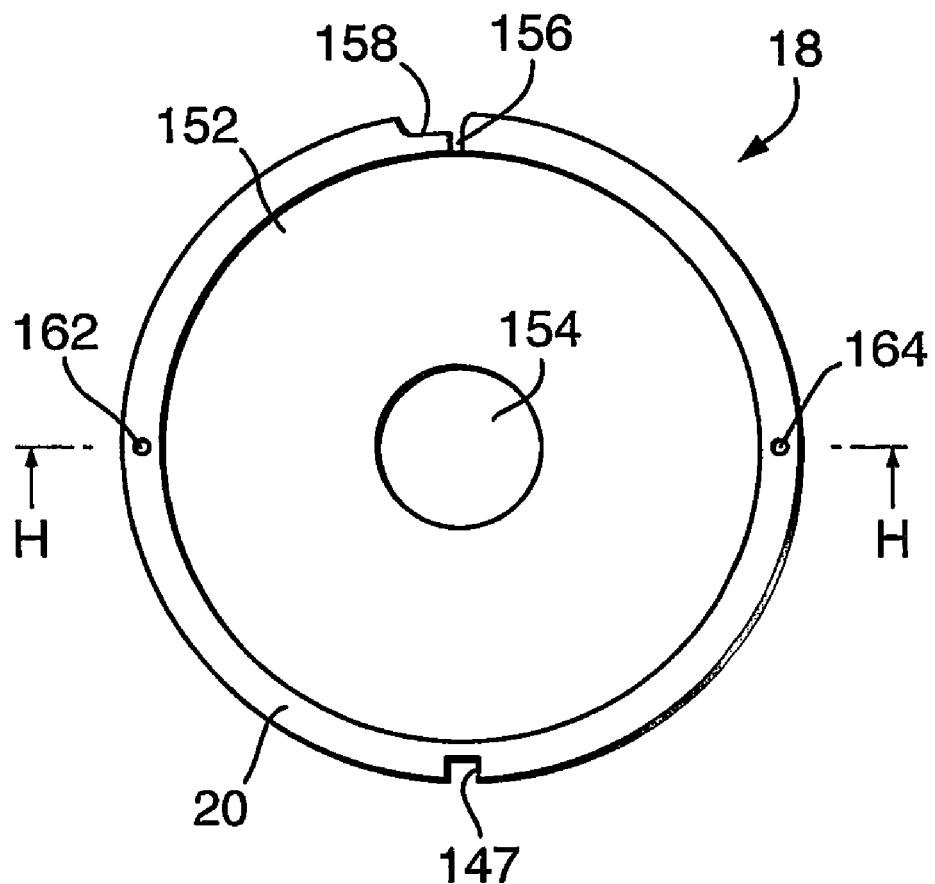
FIG. 15 is a top plan view of a spring drum of the inhaler device shown in FIG. 1.
Figure 16:
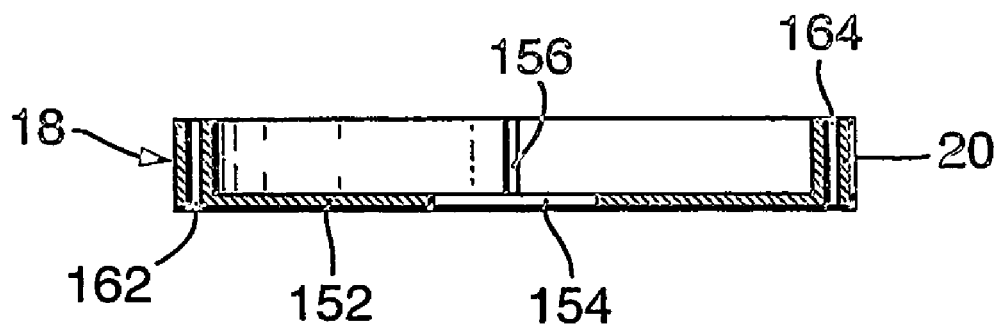
FIG. 16 is a cross-sectional side view of the spring drum of FIG. 15 taken along line H-H of FIG. 15.

The spring drum member 18 is shown in FIGS. 15 and 16 of the accompanying drawings. The drum 18 has a circular dish shape with an annular wall 20 upstanding from the circumferential perimeter of a circular base 152. An aperture 154 is positioned in the base 152 concentrically with the annular wall 20. In the assembled inhaler device 2 the stud 54 extends through the aperture 154. A slot 156 extends through the full thickness and depth of the annular wall 20 into a recess 158 in the radially outer surface of the wall 20. In the assembled inhaler device 2, an end 160 of the torsion spring 16 extends through the slot 156 and locates in the recess 158 flush with the radially outer surface of the wall 20. The end 160 of the spring 16 is thereby fixed relative to the spring drum 18.

Finally with respect to the spring drum 18, two holes 162, 164 extend through the full depth of the annular wall 20 and are located diametrically opposite one another. It will be understood therefore that the holes 162, 164 extend in a direction parallel with the rotary axis 48. The longitudinal axis of the holes 162, 164 align with the longitudinal axis of corresponding holes 166, 168 in the top body portion 4. The four holes 162, 164, 166, 168 are used during the assembly of the inhaler device 2 rather than during actual operation of the inhaler device 2. In the assembled inhaler device 2, the cartridge 12 is held by pins 34 against a biasing force applied to the cartridge 12 by the torsion spring 16. The rotary force applied to the cartridge 12 by the spring 16 is reacted against the top body portion 4 (as will be described hereinafter). However, in order to hold the cartridge 12 in position relative to the top body portion 4 against the spring bias during assembly of the inhaler device 2 (i.e. before the pins 34 have engaged with the radial projections 144 of the cartridge 12), a wire or other rigid tool is pushed through aligned holes 162, 164, 166, 168 of the drum 18 and top body portion 4. In this way, relative rotation of the drum 18 and top body portion 4 is prevented (despite the bias of the torsion spring 16). Once the inhaler device 2 is fully assembled and the cartridge 12 is prevented from rotating by means of a pin 34, the wire or tool may be removed from each pair of aligned holes 162, 164, 166, 168.

Figure 17:
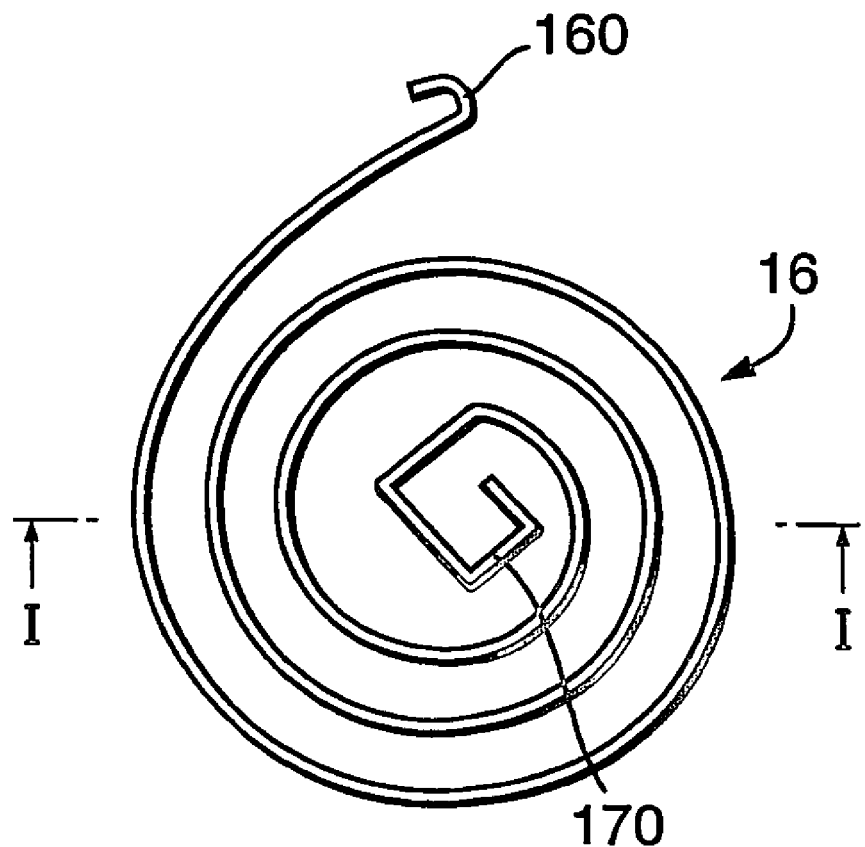
FIG. 17 is a top plan view of a spiral torsion spring of the inhaler device shown in FIG. 1.
Figure 18:
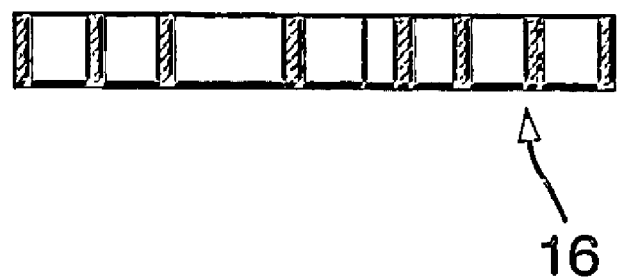
FIG. 18 is a cross-sectional side view of the spiral torsion spring of FIG. 17 taken along line I-I of FIG. 17.

The torsion spring 16 is shown in FIGS. 17 and 18 of the accompanying drawings. A first end 160 of the spring 16 is provided with a U-shaped hook which locates in the recess 158 of the spring drum 18 as previously described. The other end 170 of the spring 16 is provided with a square, rectangular or any other non-circular shape for locating about a corresponding similarly shaped portion 172 of the top body portion 4. The second end 170 of the spring 16 locates about said portion 172 of the top body portion 4 so as to remain rotationally fixed to said portion 172. Other suitable means for retaining the first end 160 of the spring 16 to the drum 18 and the second end 170 of the spring 16 to the top body portion 4 may be provided.

Figure 19:
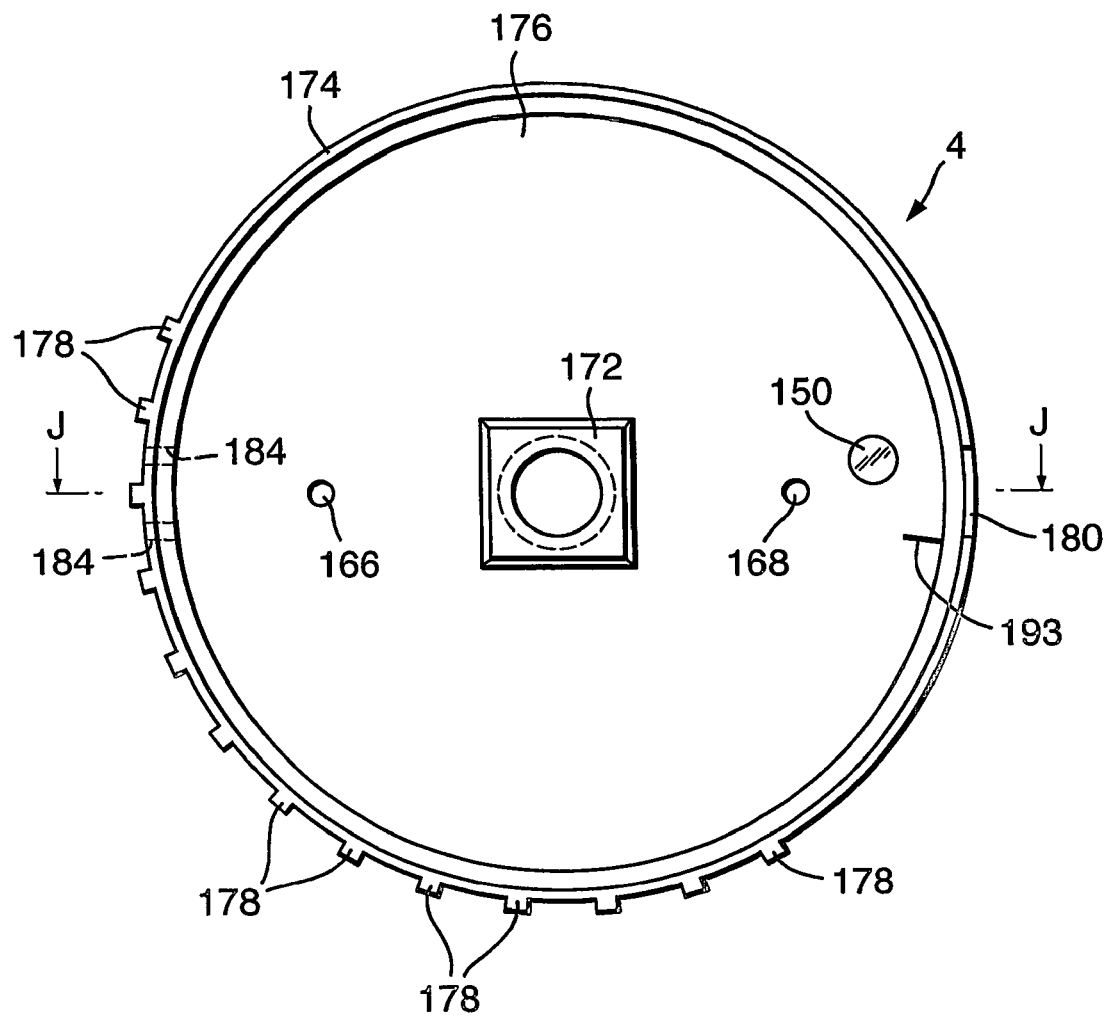
FIG. 19 is a bottom plan view of a top body portion of the inhaler device shown in FIG. 1.
Figure 20:
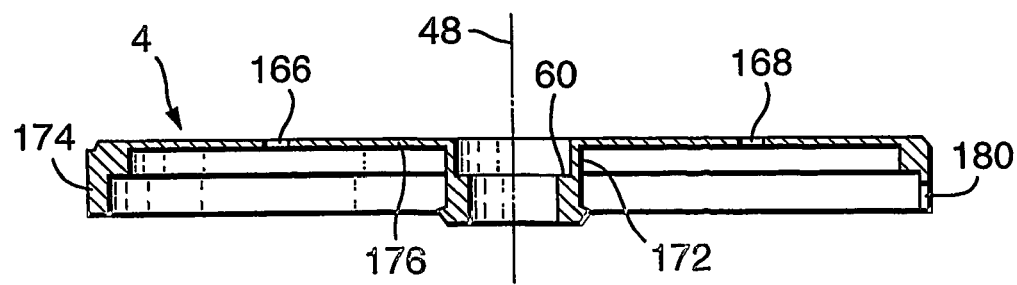
FIG. 20 is a cross-sectional side view of the top body portion of FIG. 19 taken along line J-J of FIG. 19.

The top body portion 4 as shown in FIGS. 19 and 20, comprises an annular wall 174 upstanding from the circumferential perimeter of a circular base 176. At least part of the radially outer surface of the annular wall 174 is provided with a plurality of ridges 178 which assist the user in gripping the top body portion 4. The bottom body portion 6 may also be provided with similar ridges. These body ridges are optional. A slot 180 also extends through the thickness of the annular wall 174. In the assembled inhaler device 2, the radially extending tube 90 of the central body portion 22 locates in the slot 180. The annular wall 174 is further provided with one or more apertures 182 through the thickness thereof so as to allow air to be admitted into the interior of the inhaler body as medicament is inhaled from the cartridge 12. Ideally, the air inlet apertures are located in the annular wall 174 so as to align with similar air inlet apertures 184 provided in the central body portion 22. In this way, incoming air is directed along the recess 120 in the central body portion 22 towards the inlet 94 of the spike 14.

Finally with respect to the top body portion 4, an aperture in the base 176 is provided concentrically with the annular wall 174 for receiving, in a snap-fitted relationship, the shoulder members 56, 58 of the stud 54.

Figure 21:
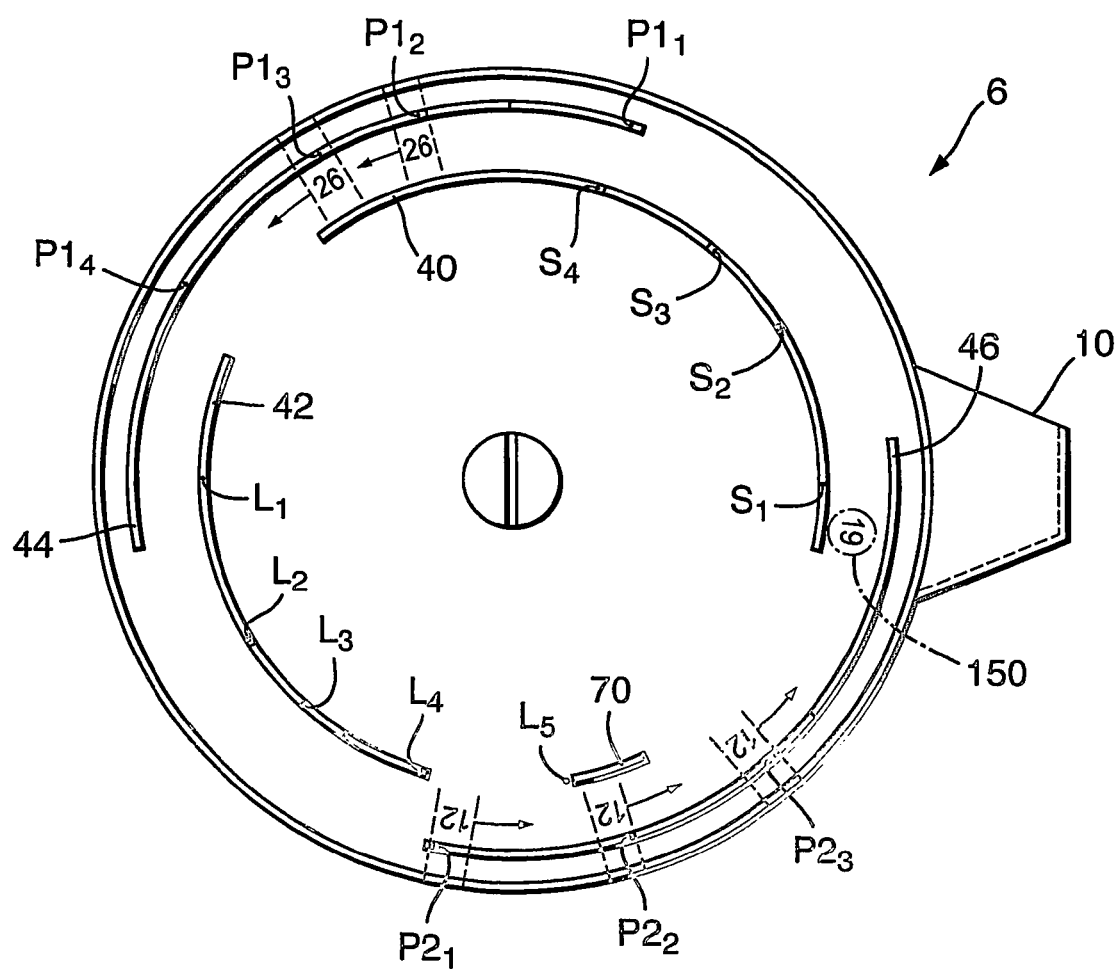
FIG. 21 is a top plan view of the bottom body portion of the inhaler device shown in FIG. 1, wherein positions are shown of various components relative to camming members as a mouthpiece cover is rotated through 90° from a mouthpiece covered position to a mouthpiece uncovered position.
Figure 22:
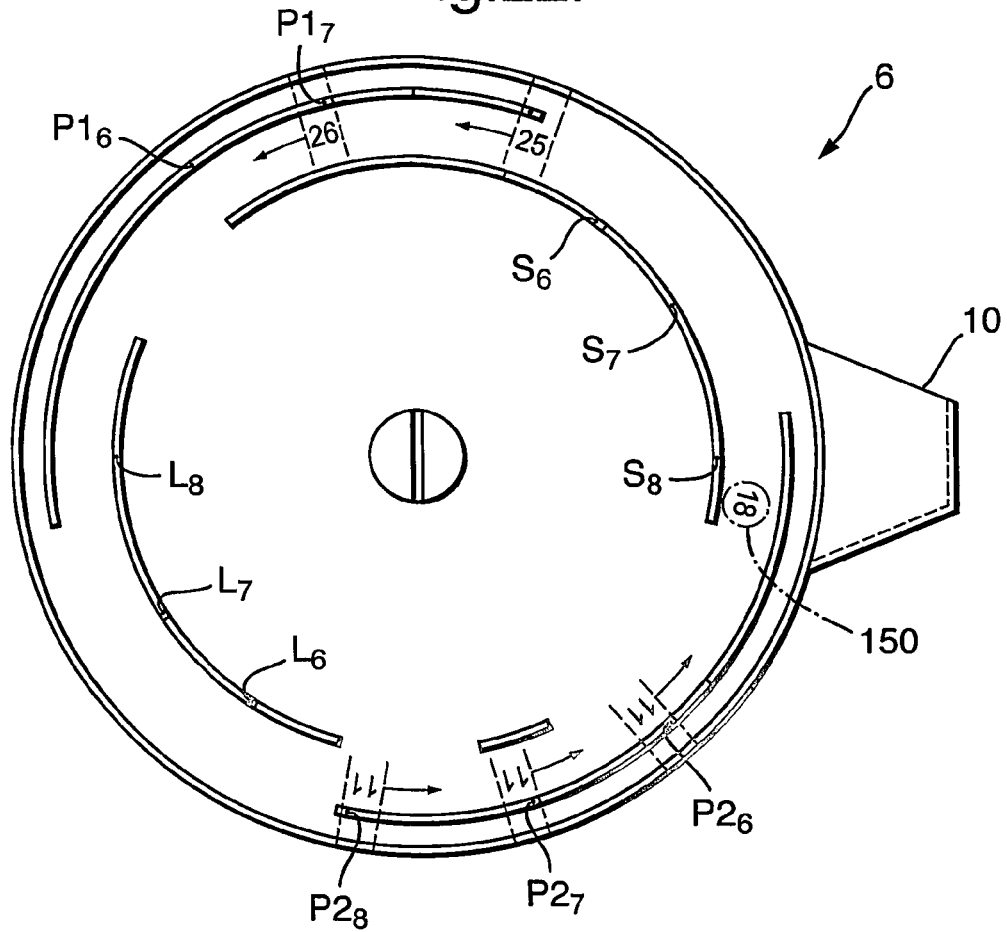
FIG. 22 is a top plan view of the bottom body portion of the inhaler device shown in FIG. 1, wherein positions are shown of said various components relative to camming members as the mouthpiece cover is rotated through 90° from the mouthpiece uncovered position to the mouthpiece covered position.

The various positions of the pins 34, spike 14 and lever 28 relative to their associated camming members 40, 42, 44, 46 and the stop projection 70 as the mouthpiece 8 and mouthpiece cover 10 are rotated relative to one another about the rotary axis 48 are shown in FIGS. 21 and 22 accompanying drawings. It will be understood from the above description, that the top body portion 4 and central body portion 22 (and the spike 14, lever 28 and pins 34 mounted thereto) rotate as a single unit about the rotary axis 48 relative to the bottom body portion 6. The cartridge 12 and torsion spring 16 similarly rotate relative to the bottom body portion 6, but also rotate relative to the top body portion 4 when the cartridge 12 advances under the biasing action of the torsion spring 16.

The principal stages of operation when rotating the top and bottom body portions 4, 6 relative to one another are described with reference to FIGS. 21 and 22 in the following table. In FIGS. 21 and 22, P1 (pin 1) refers to a first pin 34, P2 (pin 2) refers to a second pin 34, L refers to the lever 28, and S refers to the spike 14. The subscripted numbers refer to the eight principal stages of operation identified in following table. It will also be understood that the pins 34, lever 28 and spike 14 move between the positions of each principal stage as a consequence of being cammed by the canning members 40, 42, 44, 46 as the top and bottom body portions 4, 6 are rotated relative to one another about the rotary axis 48.

Movement from a Mouthpiece Covered Configuration to a Mouthpiece Uncovered Configuration (FIG. 21):
(1) Mouthpiece fully covered—Pin 1 is retracted from cartridge
  Pin 2 is extended into cartridge dose compartment 12 and locks the cartridge against spring bias
  Lever is extended so as to retract the spike (i.e. the medicament extraction facilitating means)
  Cartridge dose compartment number 19 is shown in the window
(2) Mouthpiece half uncovered—Pin 1 is extended into cartridge dose compartment 26 but is not locking the cartridge against spring bias
  Pin 2 is extended into cartridge dose compartment 12 and locks the cartridge against spring bias
  Spike is retracted from cartridge
  Lever is extended so as to retract the spike
  The same cartridge dose compartment number 19 is shown in the window
(3) Mouthpiece three quarters-uncovered
  Pin 1 is extended into cartridge dose compartment 26 and cartridge against spring bias
  Pin 2 is retracted from cartridge and is located adjacent the next cartridge dose compartment 11
  Spike is retracted from cartridge
  Lever is spaced from lever cam so as to allow extension of spike into cartridge
  Cartridge dose compartment number is changing in window—no number shown
  The cartridge dose compartment previously shown in the window is aligned with the spike
(4) Mouthpiece fully uncovered—Pin 1 is as in (3)
  Pin 2 is as in (3)
  Spike has pierced and extended through the foil of the aligned cartridge dose compartment
  Lever is as in (3)
  The cartridge dose compartment number in the window is as in (3)
(5) Continued rotation of bottom body portion and mouthpiece cover on the one hand relative to the central/top body portions and mouthpiece on the other hand is limited by abutment of the lever against a stop projection extending upwardly from the bottom body portion. Maximum relative angular movement is 90°.

Movement from a Mouthpiece Uncovered Configuration to a Mouthpiece Covered Configuration (FIG. 22):
(6) Mouthpiece fully uncovered—Pin 1 is as in (3)
  Pin 2 is as in (3)
  a Spike is located in cartridge as in (3), but is spaced from spike cam so as to allow retraction of spike from the cartridge
  Lever is engaged with lever cam
  The cartridge dose compartment number in the window is as in (3)
(7) Mouthpiece half covered (same relative angular position as for (2) except that pin 1 rather-than pin 2 locks the cartridge against spring bias)
  Pin 1 is extended into cartridge dose compartment 26 and locks cartridge against spring bias
  Pin 2 is extended into cartridge dose 11 but is not locking the cartridge against spring bias
  Spike is retracted from cartridge
  Lever is extended so as to retract the spike
  The cartridge dose compartment number in the window is as in (3).
(8) Mouthpiece fully covered (same as (1) except that the cartridge has moved on by one-dose)
  Pin 1 is retracted from cartridge
  Pin 2 is extended into cartridge dose 11 and locks the cartridge against spring bias
  Spike is retracted from cartridge
  Lever is extended so as to retract the spike
  Cartridge dose compartment number 18 is shown in the window As described in relation to the accompanying drawings, the inhaler device 2 is oriented so that the medicament extraction facilitating means (spike 14) moves upwardly from a retracted position to an extended position. As already discussed, the spike 14 thereby pierces a downwardly facing surface of a cartridge compartment 140. However, in use of the inhaler device 2, it is preferable for the inhaler device 2 to be rotated through 180° so as to be oriented in such a way that the spike 14 moves in a downward direction when moving from the retracted position to the extended position. As such, it will be understood that the top body portion 4 will be located below the bottom body portion 6. In other words, in use, it is desirable for the inhaler device 2 to be oriented the other way up to the position shown in FIG. 1. One notable reason for this preferred use orientation is that medicament in a cartridge compartment will move under the action of gravity away from the compartment surface to be pierced by the spike 14. Medicament in a pierced compartment 140 will not then tend to collect around the spike 14 but will remain slightly spaced from the inlet 100 of the spike 14. This arrangement allows medicament to be inhaled more readily.

The present invention is not limited to the specific embodiments described above. Further modifications and suitable materials will be apparent to a reader skilled in the art.

By way of example of further embodiments, it will be understood that, although the top and bottom body portions 4, 6 are described as being rotatable relative to one another by 90°, the arrangement of the camming members 40, 42, 44, 46 and stop projection 70 (and associated components) may be such that these body portions 4, 6 must be rotated relative to one another by more or less than 90° (e.g. 45°) in order to advance and pierce a cartridge compartment 140. It will appreciated however that the relative rotation of the top and bottom body portions 4, 6 must be sufficient to allow the mouthpiece 8 to become free of the mouthpiece cover 10. Alternatively, the mouthpiece cover 10 may be provided as a separate component which is entirely removed from the remainder of the inhaler device 2 when the mouthpiece 8 is uncovered for use. In a yet further alternative arrangement, the mouthpiece cover may be rotationally fixed (perhaps as a flap by means of a hinge and ideally to the mouthpiece 8) so as to allow the mouthpiece 8 to be opened without relative movement of the top and bottom body portions 4, 6.

Figure 23:
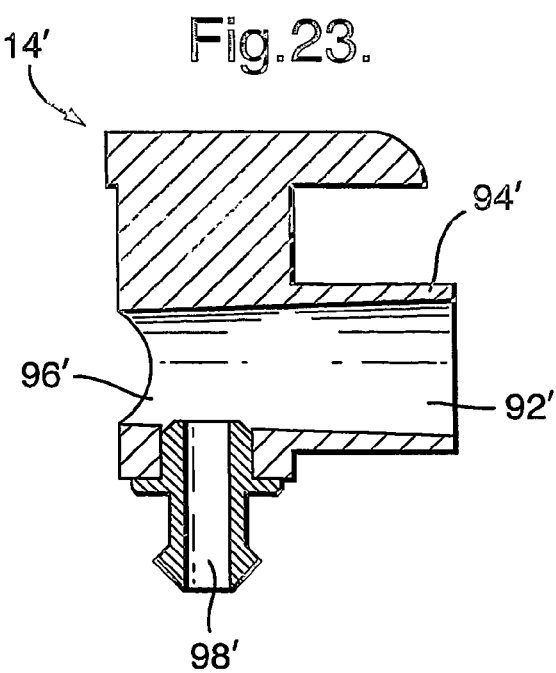
FIG. 23 is a cross-sectional side view of an alternative medicament extraction facilitating means.

In a yet further embodiment of the present invention, the converging and diverging passageways of the venturi within the spike 14 may be arranged so as to provide less of a restriction. In others words, the first fluid passageway 92 of the spike 14 may converge to a lesser extent than that shown in FIG. 7 of the accompanying drawings. The angle of convergence and divergence of the two cones of the venturi may be varied as appropriate. It is however desirable for the restriction adjacent the second fluid passageway 98 to be of a larger diameter than the second fluid passageway 98. An alternative spike 14' is shown in FIG. 23 of the accompanying drawings. With reference to this figure, it will be seen that the first fluid passageway 92' converges from the inlet 94' to the outlet 96'. The first fluid passageway 92' does not diverge in the direction of fluid flow to the outlet 96'.

Furthermore, in an alternative embodiment, the indicia indicating to a user the number of remaining cartridge compartments 140 may be provided on the cartridge 12 or the drum member 18 so as to be visible to a user through the circular side wall of the inhaler body. An appropriate window may be provided in the side wall of the inhaler body so that the indicia to be presented to a user is visible. It will be understood that this arrangement will allow indicia to be readily viewed by user when the inhaler device 2 is placed in the use orientation. The indicia may be provided on the radially outer circumferential wall of the cartridge 12 (perhaps on each of the cartridge projections 144) or may be presented on arms extending radially from the drum member 18. It will be understood however that the provision of a counter is optional.

The invention claimed is:

1. An inhaler device comprising first and second components movable relative to one another; means for receiving a medicament cartridge comprising a plurality of compartments containing medicament; medicament extraction facilitating means for locating adjacent a compartment of a received cartridge and thereby allowing an extraction of medicament therefrom; and operating means which, when activated by a user, advances a cartridge compartment of a received cartridge into a predetermined position relative to the medicament extraction facilitating means and extends the medicament extraction facilitating means into a position adjacent said advanced compartment for allowing medicament extraction upon inhalation by a user; wherein the operating means is mounted relative to said first and second components so as to be activated in response to said first and second components being moved relative to one another by a user, and wherein the operating means comprises biasing means for applying a force to a received cartridge which, on activation of the operating means, advances said compartment towards said predetermined position; the inhaler device being characterised in that the cartridge receiving means and the cartridge biasing means are secured to said first component, and in that the operating means further comprises two pins which are each further secured to said first component so as each to be movable between an extended position, in which the respective pin is engageable with a received cartridge so as to limit the cartridge advancement caused by said biasing force, and a retracted position, in which the respective pin is spaced from a received cartridge so as to not limit cartridge advancement.

2. An inhaler device as claimed in claim 1, wherein the operating means further comprises two camming members secured to said second component which are each arranged so as to move a different one of the two pins in response to said first and second components being moved relative to one another by a user.

3. An inhaler device as claimed in claim 2, wherein said two pin camming members are arranged so as to ensure at least one pine is located in the extended position regardless of the position of said first component relative to said second component.

4. An inhaler device as claimed in claim 3, wherein a space is provided between a medicament cartridge and a pin moved from a retracted position into engagement therewith, the space being such that, when a first pin moves from an extended position into a retracted position, the space between the cartridge and a second pin engaged therewith is closed as the cartridge advances under the bias of the biasing means.

5. An inhaler device as claimed in claim 1, wherein the operating means retracts the medicament extraction facilitating means from adjacent said advanced compartment when further activated by a user, wherein the operating means is mounted relative to said first and second components so as to be further activated in response to said first and second components being moved relative to one another by a user.

6. An inhaler device as claimed in claim 1, wherein the medicament extraction facilitating means is secured to said first component so as to be movable between an extended position, in which the extraction facilitating means is located adjacent a cartridge compartment for allowing medicament extraction therefrom, and a retracted position, in which the extraction facilitating means is spaced from said cartridge compartment so as to not limit cartridge advancement; and the operating means comprises camming means secured to said second component which is arranged so as to move the extraction facilitating means in response to said first and second components being moved relative to one another by a user.

7. An inhaler device as claimed in claim 6, wherein said camming means comprises two separate camming members of which moves the extraction facilitating means towards the extended position and a second of which moves the extraction facilitating means towards the retracted position.

8. An inhaler device as claimed in claim 7, wherein the operating means comprises a lever pivotally secured to said first component and connecting the extraction facilitating means to one of said two separate caroming members.

9. An inhaler device as claimed in claim 1, further comprising counting means for indicating to a user the number of compartments remaining to be advanced.

10. An inhaler device as claimed in claim 9, wherein the counting means comprises a member provided with indicia and means for moving said member across a window when a compartment is advanced.

11. An inhaler device as claimed in claim 1, further comprising a mouthpiece secured to one of said components and in fluid communication with the medicament extraction facilitating means, and a mouthpiece cover secured to the other of said components.

12. An inhaler device as claimed in claim 1, comprising a mouthpiece and a mouthpiece cover for covering the mouthpiece.

13. An inhaler device as claimed in claim 12, wherein the mouthpiece cover is fixed to the mouthpiece so as to allow relative rotational movement of the mouthpiece and mouthpiece cover between a first configuration, in which the mouthpiece is covered, and a second configuration, in which the mouthpiece is uncovered.

14. An inhaler device as claimed in claim 1, wherein the extraction facilitating means comprises a fluid passage defining a venturi.

15. An inhaler device as claimed in claim 1, wherein the extraction facilitating means comprises means for piercing a compartment.

16. An inhaler device as claimed in claim 1, wherein means are provided for preventing advancement of the cartridge once the medicament extraction facilitating means has been located adjacent each compartment of the cartridge.

17. An inhaler device as claimed in claim 1, wherein a stop member is provided on the cartridge which, when engaged with a stop member provided on one of said first and second components, prevents movement of the cartridge further than the last dose.

18. An inhaler device comprising first and second components movable relative to one another; means for receiving a medicament cartridge comprising a plurality of compartments containing medicament; medicament extraction facilitating means for locating adjacent at compartment of a received cartridge and thereby allowing an extraction of medicament therefrom; and operating means which, when activated by a user, advances a cartridge compartment of a received cartridge into a predetermined position relative to the medicament extraction facilitating means and extends the medicament extraction facilitating means into a position adjacent said advanced compartment for allowing medicament extraction upon inhalation by a user; wherein the operating means is mounted relative to said first and second components so as to be activated in response to said first and second components being moved relative to one another by a user, wherein the medicament extraction facilitating means is secured to said first comronent so as to be movable between an extended position, in which the extraction facilitating means is located adjacent a cartridge compartment for allowing medicament extraction therefrom, and a retracted position, in which the extraction facilitating means is spaced from said cartridge compartment so as to not limit cartridge advancement; and the operating means comprises camming means secured to said second component which is arranged so as to move the extraction facilitating means in response to said first and second components being moved relative to one another by a user.

19. An inhaler device as claimed in claim 18, wherein said camming means comprises two separate camming members, a first of which moves the extraction facilitating means towards the extended position and a second of which moves the extraction facilitating means towards the retracted position.

20. An inhaler device as claimed in claim 19, wherein the operating means comprises a lever pivotally secured to said first component and connecting the extraction facilitating means to one of said two separate caroming members.

21. An inhaler device as claimed in claim 18, further comprising counting means for indicating to a user the number of compartments remaining to be advanced.

22. An inhaler device as claimed in claim 21, wherein the counting means comprises a member provided with indicia and means for moving said member across a window when a compartment is advanced.

23. An inhaler device as claimed in claim 18, further comprising a mouthpiece secured to one of said components and in fluid communication with the medicament extraction facilitating means, and a mouthpiece cover secured to the other of said components.

24. An inhaler device as claimed in claim 18, comprising a mouthpiece and a mouthpiece cover for covering the mouthpiece.

25. An inhaler device as claimed in claim 24, wherein the mouthpiece cover is fixed to the mouthpiece so as to allow relative rotational movement of the mouthpiece and mouthpiece cover between a first configuration, in which the mouthpiece is covered, and a second configuration, in which the mouthpiece is uncovered.

26. An inhaler device as claimed in claim 18, wherein the extraction facilitating means comprises a fluid passage defining a venturi.

27. An inhaler device as claimed in claim 18, wherein the extraction facilitating means comprises means for piercing a compartment.

28. An inhaler device as claimed in claim 18, wherein means are provided for preventing advancement of the cartridge once the medicament extraction facilitating means has been located adjacent each compartment of the cartridge.

29. An inhaler device as claimed in claim 18, wherein a stop member is provided on the cartridge which, when engaged with a stop member provided on one of said first and second components, prevents movement of the cartridge further than the last dose.

30. An inhaler device comprising first and second components movable relative to one another; means for receiving a medicament cartridge comprising a plurality of compartments containing medicament; medicament extraction facilitating means for locating adjacent a compartment of a received cartridge and thereby allowing an extraction of medicament therefrom; and operating means which, when activated by a user, advances a cartridge compartment of a received cartridge into a predetermined position relative to the medicament extraction facilitating means and extends the medicament extraction facilitating means into a position adjacent said advanced compartment for allowing medicament extraction upon inhalation by a user; wherein the operating means is mounted relative to said first and second components so as to be activated in response to said first and second components being moved relative to one another by a user, and further comprising a mouthpiece secured to one of said components and in fluid communication with the medicament extraction facilitating means, and a mouthpiece cover secured to the other of said components.

31. An inhaler device as claimed in claim 30, further comprising counting means for indicating to a user the number of compartments remaining to be advanced.

32. An inhaler device as claimed in claim 31, wherein the counting means comprises a member provided with indicia and means for moving said member across a window when a compartment is advanced.

33. An inhaler device as claimed in claim 30, wherein the extraction facilitating means comprises a fluid passage defining a venturi.

34. An inhaler device as claimed in claim 30, wherein the extraction facilitating means comprises means for piercing a compartment.

35. An inhaler device as claimed in claim 30, wherein means are provided for preventing advancement of the cartridge once the medicament extraction facilitating means has been located adjacent each compartment of the cartridge.

36. An inhaler device as claimed in claim 30, wherein a stop member is provided on the cartridge which, when engaged with a stop member provided on one of said first and second components, prevents movement of the cartridge further than the last dose.

37. An inhaler device comprising first and second components movable relative to one another; means for receiving a medicament cartridge comprising a plurality of compartments containing medicament; medicament extraction facilitating means for locating adjacent a compartment of a received cartridge and thereby allowing an extraction of medicament therefrom; and operating means which, when activated by a user, advances a cartridge compartment of a received cartridge into a predetermined position relative to the medicament extraction facilitating means and extends the medicament extraction facilitating means into a position adjacent said advanced compartment for allowing medicament extraction upon inhalation by a user; wherein the operating means is mounted relative to said first and second components so as to be activated in response to said first and second components being moved relative to one another by a user, and further comprising a mouthpiece and a mouthpiece cover for covering the mouthpiece, wherein the mouthpiece cover is fixed to the mouthpiece so as to allow relative rotational movement of the mouthpiece and mouthpiece cover between a first configuration, in which the mouthpiece is covered, and a second configuration, in which the mouthpiece is uncovered.

38. An inhaler device as claimed in claim 37, further comprising counting means for indicating to a user the number of compartments remaining to be advanced.

39. An inhaler device as claimed in claim 38, wherein the counting means comprises a member provided with indicia and means for moving said member across a window when a compartment is advanced.

40. An inhaler device as claimed in claim 37, wherein the extraction facilitating means comprises a fluid passage defining a venturi.

41. An inhaler device as claimed in claim 37, wherein the extraction facilitating means comprises means for piercing a compartment.

42. An inhaler device as claimed in claim 37, wherein means are provided for preventing advancement of the cartridge once the medicament extraction facilitating means has been located adjacent each compartment of the cartridge.

43. An inhaler device as claimed in claim 37, wherein a stop member is provided on the cartridge which, when engaged with a stop member provided on one of said first and second components, prevents movement of the cartridge further than the last dose.

* * * * *